United States Patent [19]
Dorziotis et al.

[11] Patent Number: 5,856,498
[45] Date of Patent: Jan. 5, 1999

[54] METHOD OF PREPARING PHOSPHODIESTERASE IV INHIBITORS

[75] Inventors: Ilias K. Dorziotis, Bridgewater; Ioannis N. Houpis, Plainfield; Jaemoon Lee, Edison; Ralph P. Volante, Cranbury, all of N.J.

[73] Assignee: Merck & Co., Inc., Rahway, N.J.

[21] Appl. No.: 931,155

[22] Filed: Sep. 16, 1997

Related U.S. Application Data

[60] Provisional application No. 60/026,250 Sep. 17, 1996.

[51] Int. Cl.⁶ .................... C07D 213/30; C07D 213/127
[52] U.S. Cl. ............................ 546/339; 546/348
[58] Field of Search ..................... 546/339, 348

[56] References Cited

FOREIGN PATENT DOCUMENTS

| | | |
|---|---|---|
| WO 9109061 | 6/1991 | WIPO . |
| WO 94/20446 | 9/1994 | WIPO . |
| WO 94/14742 | 6/1995 | WIPO . |
| WO 95/17386 | 6/1995 | WIPO . |
| WO 97/38976 | 10/1997 | WIPO . |

OTHER PUBLICATIONS

J. A. Beavo & D. H. Reifsnyder, *Trends Pharmacol. Sci*, II, pp. 150–155 (1990).
M. Conti et al., *Endocrine*, Rev. 12, pp. 218–234 (1991).
S. A. Harrison et al., *Mol. Pharmacol.*, 29, pp. 506–514 (1986).
P. G. Gillespie et al, *Mol Pharmacol.*, 36, pp. 773–781 (1989).
H. H. Schneider et al, *Eur. J. Pharmacol.*, 127, pp. 105–115 (1986).
P.T. Peachell et al., *J. Immunol.*, 148, pp. 2503–2510 (1992).
Dai et al., B. J., *Pharmacol.*, 103, pp. 1399–1406 (1991).
C. K. M. Heo et al., *J. Org. Chem.*, 57, pp. 3570.
A. R. Katritzky et al., *J. Org. Chem*, 51, pp. 4914 (1986).
J. Y. L Chung, et al., *J. Org Chem.*, 61, pp. 3176 (1996).
V. Boekelheide et al., *J. Am. Chem. Soc.*, 71, pp. 879 (1949).
V. Boekelheide et al., *J. Am. Chem. Soc.*, 73, pp. 2356 (1951).
W. C. Frank et al., *J. Org Chem.*, 43, pp. 2947 (1978).
Kruft, V. et al., *Anal. Biochem.* 193, 306 (1991).

*Primary Examiner*—Bernard Dentz
*Attorney, Agent, or Firm*—Sylvia A. Ayler; Mark R. Daniel

[57] ABSTRACT

This invention is concerned with a novel process for the preparation of a compound of structural formula I

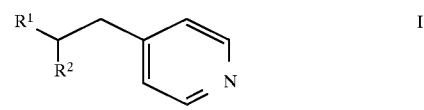

wherein $R^1$ and $R^2$ independently are aryl, $C_{2-15}$ alkenyl or $C_{1-15}$ alkyl, either unsubstituted or substituted with one or three substituents, which can be the same or different, selected from the group consisting of $R^a$, wherein $R^a$ belongs to a group consisting of $C_{1-6}$ alkyl, aryl, halo, $-N(R^3)_2$, $-NO_2$, $-CN$, $-OR^3$, $-C_{3-6}$ cycloalkoxy, $-CO(R^3)$, $-COOR^3$, $SO_2R^3$ and $-SR^3$; wherein R3 is selected from the group consisting of hydrogen, $C_{1-6}$ alkyl, $C_{2-6}$ alkenyl and aryl, said alkyl, alkenyl or aryl optionally substituted with 1 to 3 groups of $R^a$, which is an important antiasthmatic agent.

6 Claims, No Drawings

METHOD OF PREPARING PHOSPHODIESTERASE IV INHIBITORS

This application claims priority from Provisional application Ser. No. 60/026,250 filed Sep. 17, 1996.

BACKGROUND OF THE INVENTION

This application is directed to an improved process for making phosphodiesterase IV inhibitors such as those described in WO 94/14742, published Jul. 7, 1994.

Many hormones and neurotransmitters modulate tissue function by elevating intra-cellular levels of adenosine 3',5'-cyclic monophosphate (cAMP). The role of cyclic AMP (cAMP) as a second messenger is well recognized. It is responsible for transducing the effects of a variety of extracellular signals, including hormones and neurotransmitters. The level of intracellular cAMP is regulated through both its synthesis by adenyl cyclases and degradation by cyclic nucleotide phosphodiesterases (PDE). PDEs form a family of at least seven enzyme isotypes (I–VII) which differ in their affinity for cAMP and/or cGMP, subcellular localisation and regulation (Beavo J. A. and Reifsnyder D. H. (1990) *Trends Pharmacol. Sci.* 11 150–155; Conti M. et al., (1991) *Endocrine Rev.* 12 218–234). The clinical effects of a number of drugs can be rationalised on the basis of their selectivity for a particular PDE isotype. For example, the cardiotonic drugs milrinone and zaprinast are PDE III and PDE V inhibitors respectively. (Harrison S. A. et al., (1986) *Mol. Pharmacol.* 29 506–514; Gillespie P. G. and Beavo J. (1989) *Mol. Pharmacol.* 36 773–781). The anti-depressant drug, rolipram functions as a selective PDE IV inhibitor. (Schneider H. H. et al., (1986) *Eur. J. Pharmacol.* 127 105–115.).

The availability of PDE isotype selective inhibitors has enabled the role of PDEs in a variety of cell types to be investigated. In particular it has been established that PDE IV controls the breakdown of cAMP in many inflammatory cells, for example, basophils (Peachell P. T. et al., (1992) *J. Immunol.* 148 2503–2510) and eosinophils (Dent G. et al., (1991) *Br. J. Pharmacol.* 103 1339–1346) and that inhibition of this isotype is associated with the inhibition of cell activation. Consequently PDE IV inhibitors are currently being developed as potential anti-inflammatory drugs particularly for the prophylaxis and treatment of asthma.

Nucleophilic conjugate additions to vinyl pyridines have received considerable attention over the last several decades. Heo, C. K. M. et al., *J. Org. Chem.* 1992, 57, 3570. The highly electrophilic double bond of this heterocycle has been used in a variety of applications such as: a pyridine-ethylenation agent for the indentification and/or purification of cysteine residues in on-line peptide sequencers, Kruft, V. et al., *Anal. Biochem.* 1991, 193, 306; a thiol protecting group, Katritzky, A. R. et al., *J. Org. Chem.* 1986, 51, 4914; a substrate in polymerization reactions useful in the rubber industry, Abraham, T. et al., patent WO 9109061 A2 910627; and a substrate in the synthesis of important pharmaceuticals, Chung, J. Y. L. et al., *J. Org. Chem.* 1996, 61, 3176.

There are a number of nucleophiles that react well with 4-vinylpyridine (or the 2-substituted derivative) ranging from soft nucleophiles, such as malonate anions, ester and amide anions, and aryl palladium reagents see Boekelheide, V. et al., *J. Am. Chem. Soc.,* 1949, 71, 879; Boekelheide, V. et al., *J. Am. Chem. Soc.,* 1951, 73, 2356 and Frank, W. C., et al., *J. Org. Chem.* 1978, 43, 2947. In contrast, addition of nucleophiles to substituted 4-vinyl pyridines has not received much attention.

A prior art process employs a synthetic strategy using 2S-bomane-010,2-sultan as a chiral auxiliary as shown below:

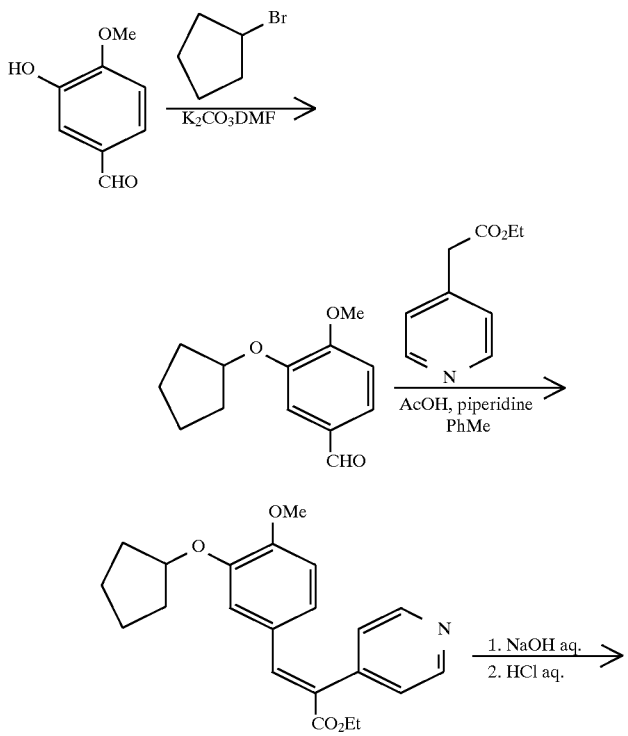

-continued
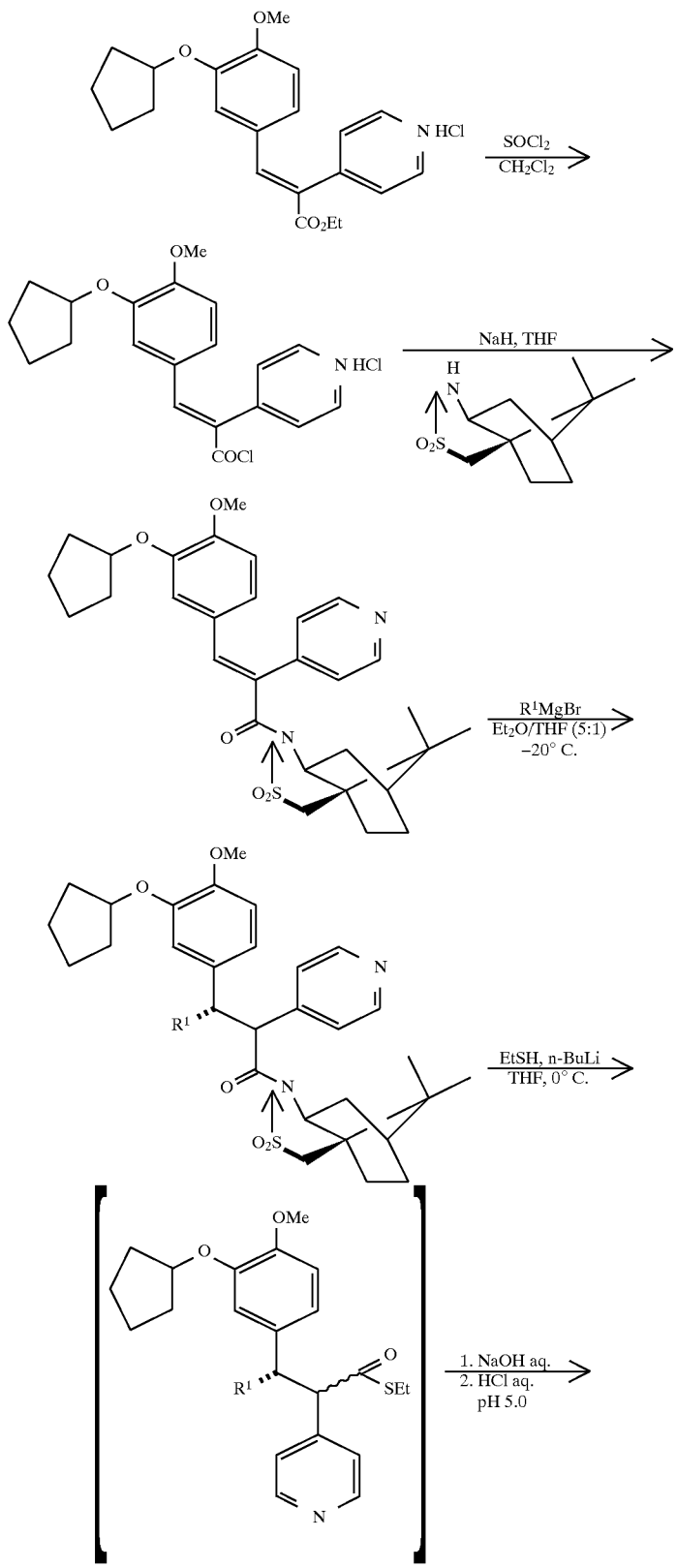

-continued

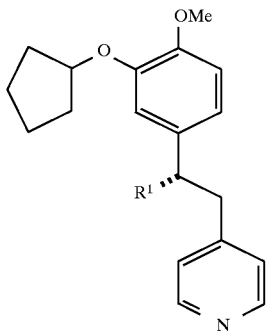

This method is not amenable to scale-up because of: a) it requires to many steps, b) the high price of the sultam; c) facile isomerization of the acid chloride during its preparation and/or the coupling reaction with the sultam, and d) extreme odor problem during the sultam cleavage using ethanethiol.

Another prior art process comprises treating the olefin 2, and a catalyst, nickel acetylacetonate, Ni(acac)2, with a slurry of the zincate, $R^1_3M$, wherein M is ZnLi or ZnMgBr, followed by reductive removal of the sulfinyl group.

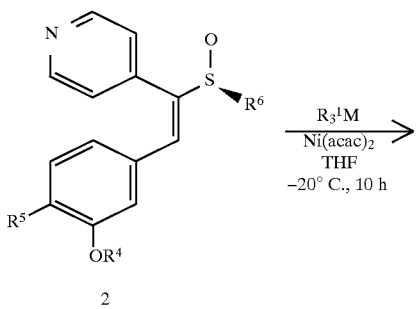

2

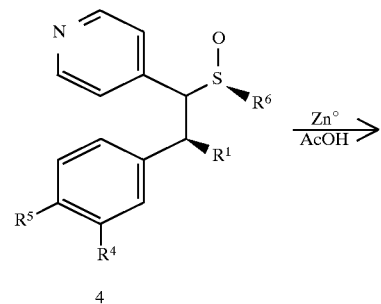

4

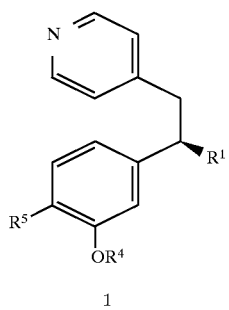

1

$R^1$ is phenyl, substituted phenyl, $C_{1-6}$ alkyl or $C_{2-6}$ alkenyl. This method also requires many steps.

Now, with the present invention there is provided a ready synthesis that produces Compound I in high yield. The process can be carried out in a few steps without the need for the introduction of activating groups.

SUMMARY OF THE INVENTION

This invention is concerned with a novel process for the preparation of a compound of structural formula I

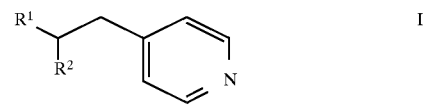

wherein

R1 and R2 independently are aryl, $C_{2-15}$ alkenyl or $C_{1-15}$ alkyl, either unsubstituted or substituted with one or three substituents, which can be the same or different, selected from the group consisting of $R^a$, $R^a$ belongs to a group consisting of $C_{1-6}$ alkyl, aryl, halo, —N$(R^3)_2$, —NO$_2$, —CN, —OR$^3$, —C$_{3-6}$ cycloalkoxy, —CO(R$^3$), —COOR$^3$, SO$_2$R$^3$ and —SR$^3$; and R3 is selected from the group consisting of hydrogen, $C_{1-6}$ alkyl, $C_{2-6}$ alkenyl and aryl, said alkyl, alkenyl or aryl optionally substituted with 1 to 3 groups of $R^a$, which is an important antiasthmatic agent.

The instant process reduces the number of steps required to produce the compounds of formula I and provides the compounds of formula I in high yield.

DETAILED DESCRIPTION OF THE INVENTION

The novel process of this invention is depicted generally in Scheme 1 below:

SCHEME 1

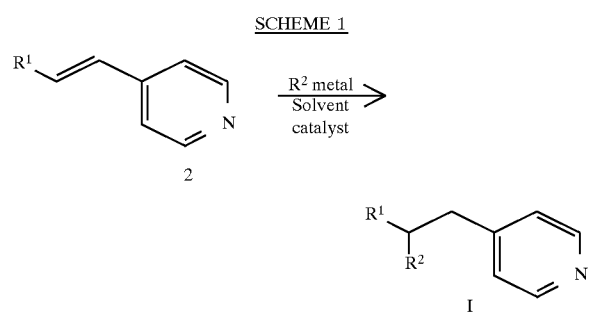

wherein $R^1$ and $R^2$ are described above.

In one aspect of the invention, preparation of a Compound of structural formula I:

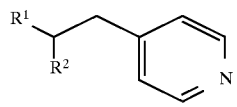

I comprises treating an intermediate 2:

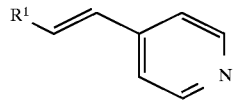

2 wherein R1 is as described above, an organometallic reagent belonging to the group consisting of a Grignard reagent ($R^2$MgX), organozincate reagent [$(R^2)_3$ZnX], a mixture of NaBH4 and $R^2$HgCl wherein $R^2$ is described above and X is Cl, Br, I, Li, MgBr, Li(Cl) or MgCl; and a nickel catalyst belonging to the group consisting of $Cl_2Ni[Ph_2P(CH_2)_2PPh_2]$, $Cl_2Ni(PPh_3)_2$, $Ni(CO_2R^2)_2$, $Ni(stearate)_2$, $Ni(cyclohexanebutyrate)_2$ and $Ni(acac)_2$; in a solvent belonging to the group consisting of toluene, THF, diethyl ether, glyme, or diglyme; mixing the resultant solution at a temperature of about 0° C. to about 65° C. to produce Compound I and isolating compound I, wherein:

R1 and R2 independently are aryl, $C_{2-15}$ alkenyl or $C_{1-15}$ alkyl, either unsubstituted or substituted with one or three substituents, which can be the same or different, selected from the group consisting of $R^a$;

$R^a$ belongs to a group consisting of $C_{1-6}$ alkyl, aryl, halo, —N($R^3$)$_2$, —NO$_2$, —CN, —OR$^3$, —C$_{3-6}$ cycloalkoxy, —CO(R$^3$), —COOR$^3$, SO$_2$R$^3$ and —SR$^3$; and R3 is selected from the group consisting of hydrogen, $C_{1-6}$ alkyl, $C_{2-6}$ alkenyl and aryl, said alkyl, alkenyl or aryl optionally substituted with 1 to 3 groups of $R^a$.

Another aspect of the invention is realized when the solvent is THF and the temperature of the solution, is heated to from about 10° C. to about 55° C.

A further aspect of the invention is realized when the temperature of the solution is heated to from about 30° C. to about 52° C. and the solvent is THF.

Yet another aspect of the invention is realized when the resultant solution is immediately heated.

Still another aspect of the invention is realized when the Grignard reagent is without β-hydrogens.

In a preferred aspect of the invention, when the organozincate reagent is used then only $Ni(acac)_2$ or $Ni(CO_2R^2)_2$ is employed.

In this application "alkyl" means straight, cyclic or branched alkyl with the indicated number of carbon atoms. "Halo" means chloro, bromo, fluoro or iodo. Aryl refers to aromatic rings which are substituted or unsubstituted e.g., phenyl, pyridyl, pyrimidinyl, thiophenyl, furanyl, imidazolyl, and like groups as well as rings which are fused, e.g., naphthyl and the like. The preferred aryl groups are phenyl and naphthyl. The term "alkoxy" refers to those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

The starting material, 2, is obtained according to the following reaction scheme:

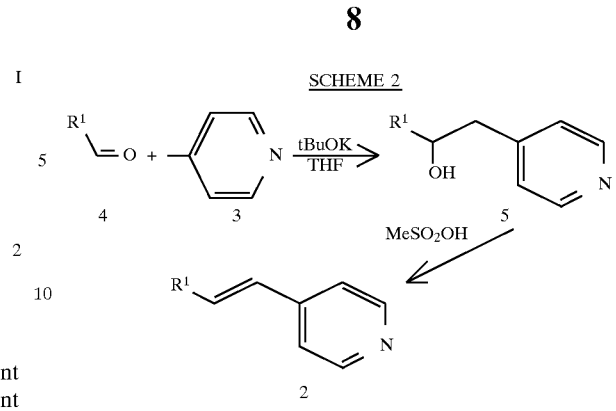

wherein $R^1$ is as described above.

Complete details for preparation of 2 are provided in the non-limiting Example that follows, which is depicted Schemes 1 and 2 above.

EXAMPLE 1

Synthesis of Substituted 4-vinylpyridine (olefin 2)

To a stirred solution of potassium t-butoxide (66.7 g, 0.60 mmol) in 600 mL of dry THF 4-picoline 3 (58 ml, 0.60 mmol) was added at −30° C. After 15 minutes, the aldehyde 4, (herein $R^1$ is p-MeO; m-CpO-phenyl) (66 g, 0.3 mmol) in 100 mL was added over 45 minutes via cannula (the reaction temperature was kept at −30° C.). The reaction was further stirred at this temperature for 1.5 hours (internal reaction temperature from about −30° to about −20° C.). At this time, the reaction was quenched by addition of aqueous, saturated NH$_4$Cl (500 ml). The mixture was extracted with ethyl acetate (2 times), dried over Na$_2$SO$_4$, and concentrated under reduced pressure. Azeotropic removal of 4-picoline with n-heptane followed by crystallization of the residue with ethyl acetate-hexanes afforded 70 g of carbinol 5.

The resulting carbinol was dissolved in ethyl acetate (700 mL) and treated with MeSO$_2$OH (50 mL at ambient temperature). The resulting mixture was heated to 65° C. and maintained at this temperature for 15 minutes. After cooling to 23° C., the reaction mixture was poured into a saturated aqueous solution of NaHCO$_3$ (500 mL) (Caution: CO2 evolution), and the resulting mixture was extracted (2 times) with ethyl acetate. The combined organic layers were dried over Na2SO4 and concentrated under reduced pressure. Recrystallization of the residue from ethyl acetate-hexane afforded the olefin 2 (60 g, 68% yield). See Scheme 2.

Synthesis of 4-[2-(3-cyclopentyloxy-4-methoxyphenyl)-2-(phenyl)ethyl]pyridine

To a stirred solution of olefin 2 (1.2 g, 4 mmol) and [1.3,-Bis(diphenylphosphino)propane]nickel (II) chloride (130 mg, 6 mol %) in THF (20 mL), phenylmagnesium chloride (2M in THF, 4.6 mL) was added at room temperature. After 2 minutes, the reaction was stirred at 48° C. for 16 hours. At this time, the mixture was allowed to cool to room temperature. A saturated solution of NH$_4$Cl was added, and the resulting mixture was extracted twice with ethyl acetate. The combined extracts were washed with brine, dried over Na$_2$SO$_4$ and concentrated under reduced pressure. Flash chromatography of the residue over silica gel with 2.5% MeOH in CH$_2$Cl$_2$ afforeded 1.417 g (95%) of the named compound.

Synthesis of Zincates

Ph$_3$ZnMgCl

A solution of ZnCl$_2$ in THF (0.5M; 4 mL; 2 mmoles) was cooled to 0° C. and treated with PhMgCl (2M in THF; 3 mL; 6 mmoles) so that the internal temperature did not exceed 10° C. The slurry was then warmed to ambient temperature and aged for 30 minutes. An extra 1 mL of THF was added at this point. The olefin 2 (288 mg; 0.98 mmoles) and Ni(acac)$_2$ (18 mg; 0.07 mmoles) were added sequentially as solids and the resulting dark solution was heated immediately to 49°–50° C. for 18 hours. The reaction was monitored by HPLC and upon completion was quenched with 1N aqueous NH$_4$Cl. The resulting mixture was partitioned with ethyl acetate and the organic layer was dried over Na$_2$SO$_4$ and concentrated under reduced pressure. The residue was chromatographed to afford 348 mg (93%) of the product.

Likewise Ph$_3$ZnLi can be made employing similar methods above.

The process of the present invention is applicable to obtain such Formula I compounds or similar compounds. The following compounds, with the respective catalyst and metal were also prepared according to Example 1.

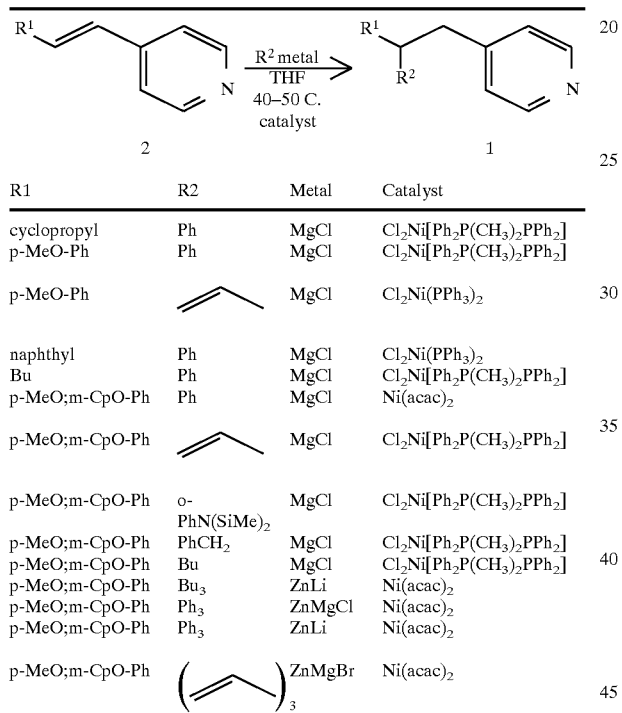

| R1 | R2 | Metal | Catalyst |
| --- | --- | --- | --- |
| cyclopropyl | Ph | MgCl | Cl$_2$Ni[Ph$_2$P(CH$_3$)$_2$PPh$_2$] |
| p-MeO-Ph | Ph | MgCl | Cl$_2$Ni[Ph$_2$P(CH$_3$)$_2$PPh$_2$] |
| p-MeO-Ph | ⌒⌒ | MgCl | Cl$_2$Ni(PPh$_3$)$_2$ |
| naphthyl | Ph | MgCl | Cl$_2$Ni(PPh$_3$)$_2$ |
| Bu | Ph | MgCl | Cl$_2$Ni[Ph$_2$P(CH$_3$)$_2$PPh$_2$] |
| p-MeO;m-CpO-Ph | Ph | MgCl | Ni(acac)$_2$ |
| p-MeO;m-CpO-Ph | ⌒⌒ | MgCl | Cl$_2$Ni[Ph$_2$P(CH$_3$)$_2$PPh$_2$] |
| p-MeO;m-CpO-Ph | o-PhN(SiMe)$_2$ | MgCl | Cl$_2$Ni[Ph$_2$P(CH$_3$)$_2$PPh$_2$] |
| p-MeO;m-CpO-Ph | PhCH$_2$ | MgCl | Cl$_2$Ni[Ph$_2$P(CH$_3$)$_2$PPh$_2$] |
| p-MeO;m-CpO-Ph | Bu | MgCl | Cl$_2$Ni[Ph$_2$P(CH$_3$)$_2$PPh$_2$] |
| p-MeO;m-CpO-Ph | Bu$_3$ | ZnLi | Ni(acac)$_2$ |
| p-MeO;m-CpO-Ph | Ph$_3$ | ZnMgCl | Ni(acac)$_2$ |
| p-MeO;m-CpO-Ph | Ph$_3$ | ZnLi | Ni(acac)$_2$ |
| p-MeO;m-CpO-Ph | (⌒)$_3$ | ZnMgBr | Ni(acac)$_2$ |

What is claimed is:

1. A process for the preparation of a compound of structural formula I:

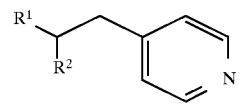

comprises treating an intermediate 2:

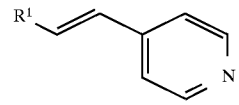

wherein R1 is as described below, an organometallic reagent belonging to the group consisting of a Grignard reagent (R$^2$MgX), organozincate reagent, a mixture of NaBH4 and R$^2$HgCl, wherein R$^2$ is described below and X is Cl, Br, I, Li, MgBr, Li(Cl) or MgCl; and a nickel catalyst belonging to the group consisting of Cl$_2$Ni, Cl$_2$Ni(PPh$_3$)$_2$, Ni(CO$_2$R$^2$)$_2$, Ni(stearate)$_2$, Ni(cyclohexanebutyrate)$_2$ and Ni(acac)$_2$; in a solvent belonging to the group consisting of toluene, THF, diethyl ether, glyme, or diglyme; mixing the resultant solution at a temperature of about 0° C. to about 65° C. to produce Compound I and isolating compound I, wherein:

R1 and R2 independently are aryl, C$_{2-15}$ alkenyl or C$_{1-15}$ alkyl, either unsubstituted or substituted with one or three substituents, which can be the same or different, selected from the group consisting of Ra;

R$^a$ belongs to a group consisting of C$_{1-6}$ alkyl, aryl, halo, —N(R$^3$)$_2$, —NO$_2$, —CN, —OR$^3$, —C$_{3-6}$ cycloalkoxy, —CO(R$^3$), —COOR$^3$, SO$_2$R$^3$ and —SR$^3$; and R3 is selected from the group consisting of hydrogen, C$_{1-6}$ alkyl, C$_{2-6}$ alkenyl and aryl, said alkyl, alkenyl or aryl optionally substituted with 1 to 3 groups of R$^a$.

2. The process of claim 1 wherein the solvent is THF and the temperature of the solution is immediately heated to from about 10° C. to about 55° C.

3. The process of claim 1 wherein the temperature of the solution is immediately heated to from about 30° C. to about 52° C.

4. The process of claim 1 wherein the resultant solution is immediately heated.

5. The process of claim 1 wherein the Grignard reagent is without β-hydrogens.

6. The process of claim 1 wherein when the organozincate reagent is used then Ni(acac)$_2$ or Ni(CO$_2$R$^2$)$_2$ is employed.

* * * * *